United States Patent
Møller et al.

(10) Patent No.: US 8,021,684 B2
(45) Date of Patent: Sep. 20, 2011

(54) HAEMOSTATIC COMPOSITION COMPRISING HYALURONIC ACID

(75) Inventors: Lene Møller, København N (DK); Kristina Devantier, Brønshøj (DK); Trine Wulff, Humlebæk (DK); Mads Christian Sabra, Copenhagen N (DK)

(73) Assignee: Ferrosan Medical Devices A/S (DE)

( * ) Notice: Subject to any disclaimer, the term of this patent is extended or adjusted under 35 U.S.C. 154(b) by 523 days.

(21) Appl. No.: 10/562,831

(22) PCT Filed: Jul. 7, 2005

(86) PCT No.: PCT/DK2005/000475
§ 371 (c)(1), (2), (4) Date: Jun. 21, 2006

(87) PCT Pub. No.: WO2006/005340
PCT Pub. Date: Jan. 19, 2006

(65) Prior Publication Data
US 2007/0009578 A1  Jan. 11, 2007

(30) Foreign Application Priority Data
Jul. 9, 2004  (DK) .............. 2004 01095

(51) Int. Cl.
A61K 9/00 (2006.01)
A61K 38/39 (2006.01)
A61K 31/728 (2006.01)

(52) U.S. Cl. ........ 424/443; 424/489; 424/492; 424/493; 424/499

(58) Field of Classification Search ............. 424/443, 424/489, 492, 493, 499
See application file for complete search history.

(56) References Cited

U.S. PATENT DOCUMENTS

| | | |
|---|---|---|
| 2,465,357 A | 3/1949 | Correll |
| 2,465,860 A | 3/1949 | Fleischmann |
| 2,558,395 A | 6/1951 | Studer |
| 3,224,434 A | 12/1965 | Molomut et al. |
| 3,678,933 A * | 7/1972 | Moore et al. ............ 604/366 |
| 3,815,580 A | 6/1974 | Oster |
| 3,869,539 A | 3/1975 | Kring et al. |
| 3,930,052 A | 12/1975 | De brou et al. |
| 4,098,728 A | 7/1978 | Rosenblatt |
| 4,265,233 A | 5/1981 | Sugitachi et al. |
| 4,280,954 A | 7/1981 | Yannas |
| 4,320,201 A | 3/1982 | Berg et al. |
| 4,492,305 A | 1/1985 | Avery |
| 4,515,637 A | 5/1985 | Cioca |
| 4,522,302 A | 6/1985 | Paikoff |
| 4,559,304 A | 12/1985 | Kasai |
| 4,655,211 A | 4/1987 | Sakamoto et al. |
| 4,696,812 A | 9/1987 | Silbering |
| 4,735,616 A | 4/1988 | Eibl et al. |
| 4,749,689 A | 6/1988 | Miyata et al. |
| 4,851,521 A | 7/1989 | Della valle et al. |
| 4,861,714 A | 8/1989 | Dean, Jr. et al. |
| 4,863,856 A | 9/1989 | Dean, Jr. et al. |
| 4,891,359 A | 1/1990 | Saferstein |
| 4,982,769 A | 1/1991 | Fournier et al. |
| 4,997,753 A | 3/1991 | Dean et al. |
| 5,024,841 A | 6/1991 | Chu et al. |
| 5,037,740 A | 8/1991 | Tanaka |
| 5,112,750 A | 5/1992 | Tanaka |
| 5,149,540 A | 9/1992 | Kunihiro et al. |
| 5,180,583 A | 1/1993 | Hedner |
| 5,356,883 A | 10/1994 | Kuo et al. |
| 5,387,208 A | 2/1995 | Ashton et al. |
| 5,394,886 A | 3/1995 | Nabai et al. |
| 5,399,361 A | 3/1995 | Song et al. |
| 5,401,511 A | 3/1995 | Margalit |
| 5,443,481 A | 8/1995 | Lee |
| 5,456,693 A | 10/1995 | Conston et al. |
| 5,462,860 A | 10/1995 | Mach |
| 5,503,848 A | 4/1996 | Perbellini et al. |
| 5,512,301 A | 4/1996 | Song et al. |
| 5,595,735 A | 1/1997 | Saferstein et al. |
| 5,643,596 A | 7/1997 | Pruss et al. |
| 5,645,849 A | 7/1997 | Pruss et al. |
| 5,660,854 A | 8/1997 | Haynes et al. |
| 5,669,934 A | 9/1997 | Sawyer |
| 5,690,675 A | 11/1997 | Sawyer et al. |
| 5,690,954 A | 11/1997 | Illum |
| 5,700,476 A | 12/1997 | Rosenthal et al. |
| 5,712,161 A | 1/1998 | Koezuka |
| 5,723,308 A | 3/1998 | Mach |
| 5,743,312 A | 4/1998 | Pfeifer |

(Continued)

FOREIGN PATENT DOCUMENTS

| | | |
|---|---|---|
| BG | 0051589 A1 | 7/1993 |
| BG | 0099900 A | 3/1997 |
| DE | 3146841 | 6/1983 |
| DE | 4119140 | 12/1992 |
| DE | 4407875 | 9/1995 |

(Continued)

OTHER PUBLICATIONS

Choi et al. 1999. Studies on Gelatin-Containing Artificial Skin: II. Preparation and Characterization of Cross-Linked Gelatin-Hyaluronate Sponge. J. Biomed. Mater. Res. 48:631-639.*

(Continued)

Primary Examiner — Taeyoon Kim
(74) Attorney, Agent, or Firm — Jonathan D. Ball; King & Spalding LLP

(57) ABSTRACT

The present invention relates to a haemostatic composition comprising a biologically absorbable material and hyaluronic acid or a derivative thereof, methods of producing such compositions and the use of these compositions. In particular the method of producing said haemostatic composition comprises treating it with dry heat at a temperature between 110-200° C.

34 Claims, No Drawings

U.S. PATENT DOCUMENTS

| | | | |
|---|---|---|---|
| 5,749,895 A | 5/1998 | Sawyer et al. |
| 5,791,352 A | 8/1998 | Reich et al. |
| 5,795,330 A | 8/1998 | Tofighi et al. |
| 5,798,091 A | 8/1998 | Trevino et al. |
| 5,823,671 A | 10/1998 | Mitchell et al. |
| 5,824,015 A | 10/1998 | Sawyer |
| 5,883,078 A | 3/1999 | Seelich et al. |
| 5,890,610 A | 4/1999 | Jansen et al. |
| 5,895,412 A | 4/1999 | Tucker |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,986,168 A * | 11/1999 | Noishiki | 424/422 |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,063,061 A | 5/2000 | Wallace et al. |
| 6,066,325 A | 5/2000 | Wallace et al. |
| 6,074,663 A | 6/2000 | Delmotte et al. |
| 6,096,309 A | 8/2000 | Prior et al. |
| 6,099,952 A | 8/2000 | Cercone |
| 6,162,241 A | 12/2000 | Coury et al. |
| 6,168,788 B1 | 1/2001 | Wortham |
| 6,218,176 B1 | 4/2001 | Berthold et al. |
| 6,261,596 B1 | 7/2001 | Li et al. |
| 6,280,727 B1 | 8/2001 | Prior et al. |
| 6,283,933 B1 | 9/2001 | D'Alessio et al. |
| 6,300,128 B1 | 10/2001 | Morota |
| 6,303,323 B1 | 10/2001 | Laskey et al. |
| 6,312,725 B1 | 11/2001 | Wallace et al. |
| 6,334,865 B1 | 1/2002 | Redmond et al. |
| 6,364,519 B1 | 4/2002 | Hughes et al. |
| 6,387,413 B1 | 5/2002 | Miyata et al. |
| 6,454,787 B1 | 9/2002 | Maddalo et al. |
| 6,458,380 B1 | 10/2002 | Leaderman |
| 6,461,325 B1 | 10/2002 | Delmottte et al. |
| 6,495,127 B1 | 12/2002 | Wallace et al. |
| 6,548,081 B2 | 4/2003 | Sadozai et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 7,052,713 B2 | 5/2006 | Stimmeder |
| 7,125,860 B1 | 10/2006 | Renier et al. |
| 7,427,607 B2 | 9/2008 | Suzuki |
| 7,435,425 B2 | 10/2008 | Qian et al. |
| 2001/0008636 A1 | 7/2001 | Yamamoto et al. |
| 2001/0038848 A1 | 11/2001 | Donda et al. |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010194 A1 | 1/2002 | Watt |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0064109 A1 | 4/2003 | Qian et al. |
| 2003/0095993 A1 | 5/2003 | Benz et al. |
| 2003/0162708 A1 | 8/2003 | Wolff |
| 2003/0181659 A1 | 9/2003 | Naranda et al. |
| 2003/0232746 A1 | 12/2003 | Lamberti et al. |
| 2004/0076647 A1 | 4/2004 | Beiring |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0214277 A1 | 9/2005 | Schaufler |
| 2005/0218541 A1 | 10/2005 | Peng et al. |
| 2005/0245905 A1 | 11/2005 | Schmidt et al. |
| 2006/0002890 A1 | 1/2006 | Hersel et al. |
| 2006/0068013 A1 | 3/2006 | DiTizio et al. |
| 2006/0115805 A1 | 6/2006 | Hansen |
| 2006/0159733 A1 | 7/2006 | Pendharkar et al. |
| 2006/0189516 A1 | 8/2006 | Yang et al. |
| 2006/0193846 A1 | 8/2006 | Stimmeder |
| 2007/0009578 A1 | 1/2007 | Moller et al. |
| 2007/0025955 A1 | 2/2007 | Lowinger et al. |
| 2007/0160543 A1 | 7/2007 | Moller |
| 2007/0264301 A1 | 11/2007 | Cleek et al. |
| 2007/0264302 A1 | 11/2007 | Cleek et al. |
| 2008/0095830 A1 | 4/2008 | Van Holten |
| 2008/0311172 A1 | 12/2008 | Schapira et al. |
| 2009/0087569 A1 | 4/2009 | Fan et al. |

FOREIGN PATENT DOCUMENTS

| | | |
|---|---|---|
| EP | 0156649 | 10/1985 |
| EP | 0 341 745 B1 | 11/1989 |
| EP | 0341745 B | 11/1989 |
| EP | 0365705 | 5/1990 |
| EP | 0372966 | 11/1990 |
| EP | 0395758 | 11/1990 |
| EP | 0478827 | 4/1992 |
| EP | 0702081 | 3/1996 |
| EP | 0737467 | 10/1996 |
| EP | 0773740 | 11/1999 |
| EP | 1 005 874 B1 | 6/2000 |
| EP | 1005874 B | 6/2000 |
| EP | 1 022 031 A1 | 7/2000 |
| EP | 1022031 A | 7/2000 |
| EP | 1044693 | 10/2000 |
| EP | 1053758 | 11/2000 |
| EP | 1140235 | 10/2001 |
| EP | 1 174 463 A1 | 1/2002 |
| EP | 1174463 A | 1/2002 |
| EP | 1258256 | 11/2002 |
| EP | 0790823 | 7/2003 |
| EP | 0891193 | 8/2003 |
| EP | 1 095 064 B1 | 6/2005 |
| EP | 1095064 | 6/2005 |
| EP | 1095064 B | 6/2005 |
| EP | 1059957 | 8/2007 |
| FR | 2679772 | 2/1993 |
| FR | 2759980 | 8/1998 |
| GB | 697603 | 9/1949 |
| GB | 648619 | 10/1951 |
| GB | 1584080 | 2/1981 |
| GB | 2266239 | 10/1993 |
| GB | 2 393 120 A | 3/2004 |
| GB | 2393120 A | 3/2004 |
| GB | 2414021 | 11/2005 |
| JP | 60214728 | 10/1985 |
| JP | 62070318 | 3/1987 |
| JP | 62221357 | 9/1987 |
| JP | 1130519 | 5/1989 |
| JP | 06254148 | 9/1994 |
| JP | 10507666 | 7/1998 |
| JP | 2002513308 | 5/2002 |

| | | |
|---|---|---|
| JP | 2004002271 | 1/2004 |
| WO | WO 8902730 | 4/1989 |
| WO | WO 90/13320 | 11/1990 |
| WO | WO 9013320 | 11/1990 |
| WO | WO 9306802 | 4/1993 |
| WO | WO 9306855 | 4/1993 |
| WO | WO 9310768 | 6/1993 |
| WO | WO 9321908 | 11/1993 |
| WO | WO-9408552 | 4/1994 |
| WO | WO 94/17840 | 8/1994 |
| WO | WO 9417840 | 8/1994 |
| WO | WO 9512371 | 5/1995 |
| WO | WO 9525748 | 9/1995 |
| WO | WO 9531955 | 11/1995 |
| WO | WO 9607472 | 3/1996 |
| WO | WO 9616643 | 6/1996 |
| WO | WO 9640033 | 12/1996 |
| WO | WO 9717023 | 5/1997 |
| WO | WO 9717024 | 5/1997 |
| WO | WO 9717025 | 5/1997 |
| WO | WO 9729792 | 8/1997 |
| WO | WO 9737694 | 10/1997 |
| WO | WO 9831403 | 7/1998 |
| WO | WO 9836784 | 8/1998 |
| WO | WO 9843092 | 10/1998 |
| WO | WO 9844963 | 10/1998 |
| WO | WO 9851282 | 11/1998 |
| WO | WO 9904828 | 2/1999 |
| WO | WO 9912032 | 3/1999 |
| WO | WO 9944901 | 9/1999 |
| WO | WO 9945938 | 9/1999 |
| WO | WO 0009018 | 2/2000 |
| WO | WO 0018301 | 4/2000 |
| WO | WO 0027327 | 5/2000 |
| WO | WO 0061201 | 10/2000 |
| WO | WO 0074742 | 12/2000 |
| WO | WO 0076533 | 12/2000 |
| WO | WO 0113956 | 3/2001 |
| WO | WO 0128603 | 4/2001 |
| WO | WO 0134206 | 5/2001 |
| WO | WO 0154735 | 8/2001 |
| WO | WO 0166161 A | 9/2001 |
| WO | WO 0197826 | 12/2001 |
| WO | WO 02/18450 A1 | 3/2002 |
| WO | WO 0218450 A | 3/2002 |
| WO | WO 0222059 | 3/2002 |
| WO | WO 0240068 | 5/2002 |
| WO | WO 02058749 | 8/2002 |
| WO | WO 03007845 | 1/2003 |
| WO | WO 03055531 | 7/2003 |
| WO | WO 03070110 | 8/2003 |
| WO | WO 03094983 | 11/2003 |
| WO | WO 2004/028583 A3 | 4/2004 |
| WO | WO 2004/035629 A3 | 4/2004 |
| WO | WO 2004028404 | 4/2004 |
| WO | WO 2004028423 | 4/2004 |
| WO | WO 2004028583 | 4/2004 |
| WO | WO 2004029095 | 4/2004 |
| WO | WO 2004030711 | 4/2004 |
| WO | WO 2004035629 | 4/2004 |
| WO | WO2004053051 | 6/2004 |
| WO | WO 2004108035 | 12/2004 |
| WO | WO 2005000265 | 1/2005 |
| WO | WO 2005009225 | 2/2005 |
| WO | WO 2005/044285 A1 | 5/2005 |
| WO | WO 2005041811 | 5/2005 |
| WO | WO 2005044285 | 5/2005 |
| WO | WO 2005062889 | 7/2005 |
| WO | WO 2006034568 | 4/2006 |
| WO | WO 2006063758 | 6/2006 |
| WO | WO 2007133699 | 11/2007 |
| WO | WO 2008051758 | 5/2008 |
| WO | WO 2008090555 | 7/2008 |
| WO | WO 2009109963 | 9/2009 |

OTHER PUBLICATIONS

Cascone et al. Collagen and hyaluronic acid based polymeric blends as drug delivery systems for the release of physiological concentrations of growth hormone. Journal of Materials Science: Materials in Medicine 5 (1994) 770-774.*

Y.S. Choi et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J. of Mat. Sci.: Materials in Medicine, vol. 12, 2001.

Laurent, et al., "Hyaluronic Acid Reduces Connective Tissue Formation in Middle Ears Filled with Absorbable Gelatin Sponge: An Experimental Study", Am. J. Otolaryngol, vol. 7, p. 181-186, 1986.

West, et al., "Efficacy of Adhesion Barriers, Resorbable Hydrogel, Oxidized Regenerated Cellulose and Hyaluronic Acid", The Journal of Reproductive Medicine, vol. 41, p. 149-154, 1996.

Soules, et al., "The Prevention of Postoperative Pelvic Adhesions: An animal study comparing barrier Methods with dextran 70", Am. J. Obstet. Gynecol., vol. 143, p. 829-834, 1982.

Sanfilippo, et al., "Comparison of Avitene, Topical Thrombin, and Gelfoam as sole Hemostatic Agent in Tuboplasties", Fertility and Sterility, vol. 33, No. 3, p. 311-316, Mar. 1980.

Maxson, et al., "Efficacy of a Modified Oxidized Cellulose Fabric in the Prevention of Adhesion Formation", Gynecol. Obstet. Invest., vol. 26, p. 160-165, 1988.

Larsson, et al., "Surgicel—An Absorbable Hemostatic Material—in Prevention of Peritoneal Adhesions in Rats", Acta Chir. Scand., vol. 144, p. 375-378, 1978.

Hill-West, et al., "Efficacy of a Resorbable Hydrogel Barrier, Oxidized Regenerated Cellulose, and Hyaluronic Acid in the Prevention of Ovarian Adhesions in a Rabbit Model", Fertility and Sterility, vol. 62, No. 3, p. 630-634, Sep. 1994.

Raftery, "Absorbable Haemostatic Materials and Intraperitoneal Adhesion Formation", Br. J. Surg., vol. 67, p. 57-58, 1980.

Reijnen, et al., "Prevention of Intra-Abdominal Abscesses and Adhesions Using a Hyaluronic Acid Solution in a Rat Peritonitis Model", Arch Surg., vol. 134, p. 997-1001, Sep. 1999.

Li, et al., "Evaluation of Esterified Hyaluronic Acid as Middle Ear-Packing Material", Arch Otolaryngol Head Neck Surg., vol. 127, p. 534-539, May 2001.

De Iaco, et al., "Efficacy of a Hyaluronan Derivative Gel in Postsurgical Adhesion Prevention in the Presence of Inadequate Hemostasis", Surgery, vol. 130, p. 60-64, 2001.

Koçak, et al., "Reduction of Adhesion Formation with Cross-linked Hyaluronic Acid After Peritoneal Surgery in Rats", Fertility and Sterility, vol. 72, No. 5, p. 873-878, Nov. 1999.

Shushan, et al., "Hyaluronic Acid for Preventing Experimental Postoperative Intraperitoneal Adhesions", Journal of Reproductive Medicine, vol. 39, p. 398-402, 1994.

Luengo, et al., "Prevention of Peritoneal Adhesions by the Combined use of Spongostan and 32% Dextran 70: an Experimental Study in Pigs", Fertility and Sterility, vol. 29, No. 4, Apr. 1978.

English Derwent abstract of Ranjane reference, Nov. 18, 1997.

Gelfoam RTM product information sheet, Jul. 2007.

Google search result showing disclosure of handled Gelfoam swab in the body of the Kelly publication, accessed online on May 11, 2009.

Kelly M. J. et al., "The value of an operative wound swab sent in transport medium in the prediction of later clinical wound infection: A controlled clinical and bacteriological evaluation", Brit. J. Surgery (1978), 65:2, pp. 81-88.

Stuart Transport medium information sheet, accessed online on May 27, 2009.

Quintavalla et al., Biomaterials Jan. 2002;23(1):109-119. Fluorescently labeled mesenchymal stem cells (MSC)maintain multilineage potential and can be detected following articular cartilage defects.

Wiesenthal et al, The Journal of Otolaryngology, 1999, vol. 28, No. 5, p. 260-265, "New method for packing the external auditory canal, middle ear space, and mastoid cavities after otologic surgery".

Drognitz et al, Indection Germany (Munich), 2006, 34 (1), p. 29-34, "Release of vancomycin and teicoplanin from a plasticized and resorbable gelatin sponge: in vitro investigation of a new antibiotic delivery system with glycopeptides".

Yuesong et al, Intern. des Services de San. des Forces Armees, Sep. 1999, vol. 72, No. 7-9, p. 194-196, "Design and experimental study of a slow-release antibiotic membrane implant in surgery wound".

Hill-West, et al., Fertility and Sterility, vol. 62, No. 3, p. 630-634, "Efficacy of a resorbable hydrogel barrier, oxidized regenerated cellulose and hyaluronic acid in the prevention of ovarian adhesions in a rabbit model".

Larsson, et al., Acta Chir. Scand., vol. 26, p. 375-378, 1978, "Surgicel—An absorbable hemostatic material—In prevention of peritoneal adhesions in rats".

Sanfilippo et al, Fertility and sterility, vol. 33, No. 3, p. 311-316, Mar. 1980, "Comparison of avitene, topical thrombin and Gelfoam, as sole hemostatic agent in tuboplasties".

Luengo, et al., Fertility and Sterility, vol. 29, No. 4, Apr. 1978, "Prevention of peritoneal adhesions by the combined use of Spongostan and 32% Dextran 70: an experimental study in pigs".

De Iaco, et al., Surgery, vol. 130, p. 60-64, 2001, "Efficacy of a Hyaluronan Derivative gel in postsurgical adhesion prevention in the presence of inadequate hemostasis".

Spence et al., cancer Feb. 1975;35(2):326-341. Cerebellar capillary hemangioblastoma: its histogenesis studied by organ culture and electron microscopy.

Dembo, M. A et al, Lech. Prep. Krovi. Tkanei, p. 139-40, 1974, "Antiseptic hemostatic preparations, their properties and study".

"FloSeal Matrix Hemosealant. Instructions for use". Accessed online Aug. 17, 2005 at http://www.ctsnet.org/file/vendors/931/pdf/140.pdf.

Sakurabayashi etal., Gastroenterological Endoscopy 30(10) Oct. 1988. Clinical evaluation of new hemostatic agent for hemostasis from biopsy wounds in the liver.

Oz et al, Ann Thorac Surg 2000, vol. 69, p. 1376-1382, 2000, "Controlled clinical trial of a novel hemostatic agent in cardiac surgery".

Wachol-Drewek et al, Biomaterials 17, p. 1733-1738, 1996, "Comparative Investigation of drug delivery of collagen implants saturated in antibiotic solutions and a sponge containing gentamicin".

Hong et al, Biomaterials, 2001, 22 (20), p. 2777-2783, "Study on gelatin-containing artificial skin IV: a comparative study on the effect of antibiotic and EGF on cell proliferation during epidermal healing".

Raftery, BR. J. Surg., vol. 67, p. 57-58, 1980, "Absorbable Haemostatic materials and intraperitoneal adhesion formation".

Shushan, et al., Journal of Reproductive Medicine, vol. 39, p. 398-402, 1994, "Hyaluronic acid for preventing experimental postoperative intraperitoneal adhesions".

Li, et al., Arch Otolaryngol Head Neck Surg., vol. 127, p. 534-539, May 2001, "Evaluation of Esterified Hyaluronic Acid as middle ear-packing material".

Kocak, et al., Fertility and Sterility, vol. 72, No. 5, p. 873-878, Nov. 1999, "Reduction of adhesion formation with cross-linked hyaluronic acid after peritoneal surgery in rats".

Hae-Won et al, J. of Biomedical Materials Research, 2005, 74B (2), p. 686-698, "Porous scaffolds of gelatin-hydroxyapatite nanocomposites obtained by biometic approach: Characterization and antibiotic drug release".

Choi YS et al, J Biomed Mater Res 1999; 48 (5), p. 631-639, "Studies on gelatin-containing artificial skin: II. Preparation and characterization of cross-linked gelatin-hyaluronate sponge".

Laurent et al, Am. J. Otolaryngol, vol. 7, p. 181-186, 1986, "Hyaluronic acid reduces connective tissue formation in middle ears filled with absorbable gelatin sponge: an experimental study".

Soules et al, Am. J. Obstet. Gynecl., vol. 143, p. 829-834, 1982, "The prevention of postoperative pelvic adhesions: An animal study comparing barrier methods with Dextran 70".

Hill et al, J. Thorac Cardiovasc Surg 1994, vol. 108, p. 1151-1152, "Use of microfibrillar collagen hemostat (Avitenet) and thrombin to achieve hemostats after median sternotomy".

Van Der Salm T.J. et al, J. of Thoracic and Cardiovascular Surgery, 1989, vol. 98, No. 4, p. 618-622, "Reduction of sternal infection by application of topical vancomycin".

Maxson et al, Gynecol. Obestet. Invest., vol. 26, p. 160-165, 1988, "Efficacy of a modified oxidized cellulose fabric in the prevention of adhesion formation".

Reijnen, et al., Arch Surg., vol. 134, p. 997-1001, Sep. 1999, "Prevention of Intra-Abdominal Abscesses and adhesions using a hyaluronic acid solution in a rat peritonitis model".

Ellegala et al, Neurosurgery, Aug. 2002, vol. 51, p. 513-516, "Use of FloSeal Hemostatic Sealant in Transsphenoidal Pituitary surgery: technical note".

West, et al., The Journal of reproductive medicine, vol. 41, p. 149-154, 1996, "Efficacy of adhesion barriers, resorbable hydrogel, oxidized regenerated cellulose and hyaluronic acid".

Changez et al, Biomaterials, 2005, vol. 26, No. 14, p. 2095-2104, "Efficacy of antibiotics-loaded interpenetrating network (IPNs) hydrogel based on poly (acrylic acid) and gelatin for treatment of experimental osteomyelitis: in vivo study".

Min et al. "Molecular Weight Changes of Sodium Hyaluronate Powder and Solution by Heat Treatment," Matrix Biology Institute, Proceedings of Hyaluronan, Oct. 11-16, 2003.

Branski et al.; "Mucosal Wound Healing in a Rabbit Model of Subglottic Stenosis"; Arch Otolaryngol Head Neck Surg, vol. 131, Feb. 2005, p. 153-157.

Purdy et al.; "Microfibrillar collagen model of canine cerebral infarction"; Stroks, vol. 20 No. 10, Oct. 1989, p. 1361-1367.

Santomaso et al.; "Powder flowability and density ratios: the impact of granules packing". Chemical Engineering Science 58 (2003) 2857-2874.

Swann; "Studies on hyaluronic acid—I. The preparation and properties of rooster comb hyaluronic acid". Biochemica et biophysica acta, 156 (1968) p. 17-30.

* cited by examiner

HAEMOSTATIC COMPOSITION COMPRISING HYALURONIC ACID

CROSS-REFERENCE TO RELATED APPLICATIONS

This application is a national stage of International Application No. PCT/DK2005/000475, filed 7 Jul. 2005, which claims benefit of Denmark Patent Application No. PA 2004 01095, filed 9 Jul. 2004. The entire contents of all the above-identified applications are incorporated herein by reference.

FIELD OF THE INVENTION

The present invention relates to a haemostatic composition comprising a biologically absorbable material, preferably gelatine, and hyaluronic acid or a derivative thereof. The haemostatic compositions described herein have superior haemostatic properties as compared to conventional compositions.

BACKGROUND OF THE INVENTION

When blood vessels are injured by physical traumas including surgical interventions, bleedings will occur. Dependent on the extent of the injury, bleedings may result in losses of blood which can affect the normal function of the individual or, in cases of bleedings occurring in osseous non-expandable cavities, the accumulation of extravasated blood may cause damages of soft tissues due to increased pressure. If bleedings are left alone they will eventually be arrested by a normally occurring physiological process characterised by a chain of events involving the combined activity of vascular, platelet, and plasma factors. This process is referred to as a physiological haemostasis, an important element of which is blood coagulation which is described below. In the case of a minor superficial bleeding, this physiological haemostasis is adequate for the arrest.

Blood coagulation may be described as occurring in the following steps.

(1) The formation of an activator of prothrombin, which is a precursor of the plasma serine protease thrombin. The prothrombin activator is a complex of an enzyme factor Xa and two cofactors: factor Va and procoagulant phospholipids, both present on the surface of activated platelets. Furthermore, the presence of calcium ions is necessary for the function of the activator.

(2) The cleavage by the above activator system of prothrombin into two fragments, one of which is the enzyme thrombin.

(3) The conversion by thrombin of the plasma precursor fibrinogen to the clotting substance fibrin. This process involves several steps, the first of which comprises the cleavage of small peptides from fibrinogen, whereby fibrin monomers are formed, which then polymerise to form insoluble fibrin polymers. As a final step, thrombin activates the plasma factor XIII, an enzyme that catalyses the formation of covalent bonds between fibrin molecules, thereby cross-linking the molecules to form a firm clot resistant to dissolution.

In the above step (1) leading to the formation of the prothrombin activator system, several plasma proteases are involved in a cascade of proteolytic events. These blood coagulation factors are currently referred to by using Roman numerals, such as factor VII, factor VIII, factor IX, factor XI, and factor XII. The cascade involves sequential proteolytic activations of the next enzyme in the cascade. Thus activated blood coagulation factors are designated by their Roman numerals followed by an "a", such as factor VIIa, factor VIIIa, factor XIIIa or factor IXa.

However, bleedings emerging from more extensive injuries, especially such injuries which involve larger arteries or when seeping bleedings occur from larger mucosal surfaces or in cavities without drainage, require the adoption of surgical and/or medical haemostatic measures. Surgical arrest of bleeding comprises ligation or suture of disrupted blood vessels, plugging by using tampons in cavities, coagulating tissue surfaces including their exposed disrupted blood vessels by heated instruments or by the application of cauterising agents or heated air. Surgical haemostasis may also be aided by the application at the injured site of appropriately sized blocks, plates, or films of biologically absorbable haemostatic sponges. Powders or flakes, which are typically wetted before application to create a paste, have also been used.

In this context, the term "sponge" is understood to mean a porous structure characterised in that the structure is reticulate and has an inner surface considerably larger than its outer surface, that it contains hollow spaces within the reticulate structure, and that it can absorb many times its own weight in liquids.

Such haemostatic sponges or compositions are useful for enhancing the arrest of bleedings in several instances of surgical interventions or other injuries such as in surgery of large abdominal organs (liver, spleen, or intestines); in lung surgery; in neurosurgery to prevent pressure damages of the cerebral or nerve tissues; in orthopaedic surgery during which extensive haemorrhages frequently occur which are difficult to arrest by other means; in vascular surgery to arrest seeping bleedings from the sites of suturing; in oral or dental surgery such as extraction of teeth; and in nose-bleeding (epistaxis).

It is currently believed that the haemostatic effect (or mode of action) of a sponge is linked to sponge porosity and the sponge's ability to absorb blood. A conventional gelatine sponge adheres to the bleeding site and absorbs approximately 45 times its own weight. Due to the uniform porosity of a conventional gelatine sponge, blood platelets are caught and the coagulation cascade is activated transforming soluble fibrinogen into a net of insoluble fibrin which stops the bleeding. Thus, a good capacity to absorb is believed essential for the mode of action of conventional gelatine sponges.

As mentioned above, a conventional gelatine sponge's ability to act as a haemostat is related to its ability to absorb, whereby the volume of the sponge inevitably will increase. However, swelling of the sponge can lead to adverse events if the sponge is not used according to the instructions. Normally, the instruction for use includes the phrase: "When placed into cavities or closed tissue spaces, minimal preliminary compression is advised and care should be exercised to avoid overpackaging. The gelatine sponge may swell to its original size on absorbing fluids creating the potential for nerve damage". Nevertheless, adverse events have taken place in the past, and the UK Medical Device Agency as well as the FDA have paid much attention to this drawback of conventional sponges.

Accordingly, there is a need for haemostatic sponges which, while maintaining a sufficient blood arresting (haemostatic) effect, swell to a much lesser extent than conventional haemostatic sponges. Evidently, such sponges would constitute a safer product.

The present invention deals with haemostatic compositions with improved properties and methods of producing said compositions.

The inventors of the present invention have surprisingly found that the haemostatic compositions of the present invention are more efficient in arresting bleeding than conventional compositions, such as Surgifoam®, Surgifoam® powder or Gelfoam® powder, i.e. the haemostatic properties of the compositions according to the invention are improved compared to conventional compositions.

Furthermore, the present inventors have solved the above-mentioned problem of swelling by incorporating hyaluronic acid (HA), or a derivative thereof, into or onto a haemostatic composition.

Surprisingly, it has been found that swelling of a haemostatic sponge according to the present invention is considerably reduced compared to conventional sponges, such as Surgifoam®. Evidently, the haemostatic sponges described herein are safer to use than conventional sponges.

The above-mentioned properties, i.e. decreased tendency to swell and improved haemostatic properties, are attributed to the presence of HA, or derivatives thereof. HA, and derivatives thereof, are known to confer anti-adhesive properties to sponges as described in e.g. Laurent et al. *Am J Otolaryngol;* 7:181-186, 1986; U.S. Pat. No. 6,548,081; U.S. Pat. No. 6,099,952; U.S. Pat. No. 5,503,848; U.S. Pat. No. 5,700,476; EP 1 022 031 A1; WO 94/17840. Nevertheless, the surprising effects of conferring improved haemostatic properties to the composition and reducing the ability of a sponge to swell, have not been described in any of the above-identified prior art documents.

In summary, the haemostatic compositions and in particular a haemostatic sponge of the present invention contain numerous advantages as compared to conventional and commercially available haemostatic compositions and sponges:

i) reduced swelling, thereby rendering the sponge safer to use, ii) improved haemostatic properties, and iii) improved anti-adhesive properties, thereby reducing post-operative adhesion of tissues.

SUMMARY OF THE INVENTION

In a first aspect, the present invention relates to a haemostatic sponge comprising a biologically absorbable material and hyaluronic acid (HA) or a derivative thereof.

In a second aspect, the present invention relates to a method of producing a haemostatic composition comprising the steps of:
  i) mixing a biologically absorbable material, hyaluronic acid or a derivative thereof and a solvent
  ii) treating the mixture obtained in step i) with dry heat at a temperature between 110-200° C.

In a third aspect, the present invention relates to a composition obtainable by the above-mentioned method.

Other aspects of the present invention are directed to methods for producing the haemostatic compositions of the invention as well as to their medical uses. These, and other, aspects will be apparent from the below disclosure and the appended claims.

DETAILED DESCRIPTION OF THE INVENTION

The general effect of haemostatic compositions is to enhance the physiological blood coagulation process thereby reducing the time elapsing from opening of the blood vessels until a firm blood clot has been formed. This period is generally referred to as "the time to haemostasis". In this context, the term "haemostatic" should be understood to mean the effect of an object or an agent, which reduces the time to haemostasis, thereby promoting haemostasis.

As indicated above, the present invention is, in its broadest aspect, directed to a haemostatic composition comprising a biologically absorbable material and hyaluronic acid (HA) or a derivative thereof.

In another embodiment the present invention relates to a haemostatic composition obtainable by a method of producing a haemostatic composition comprising the steps of:
  i) mixing a biologically absorbable material and hyaluronic acid or a derivative thereof and a solvent
  ii) treating the mixture obtained in step i) with dry heat at a temperature between 110-200° C.

The particulars of this method may be as described below.

In a particular embodiment of the present invention said composition may be in the form of a sponge, i.e. the haemostatic composition may be a sponge, wherein the term "sponge" is understood to mean a porous structure characterised in that the structure is reticulate and has an inner surface considerably larger than its outer surface, that it contains hollow spaces within the reticulate structure, and that it can absorb many times its own weight in liquids.

The biologically absorbable material may be any material which is known to be suitable for preparation of sponges, powders or flakes and, at the same time, being biologically absorbable. Examples of suitable biologically absorbable materials include gelatine, collagen, chitin, chitosan, alginate, cellulose, e.g. oxidised cellulose, oxidised regenerated cellulose, carboxymethylcellulose (CMC) or hydroxyethylcellulose (HEC), polyglycolic acid, polyacetic acid, derivatives thereof and mixtures thereof. It will be understood that various forms thereof, such as linear or cross-linked forms, salts, esters and the like may also be used as the biologically absorbable material to be included in the haemostatic sponges of the invention. In one embodiment the biologically absorbable material may be solid, wherein the term "solid" refers to the thermodynamic phase of the compound.

"Biologically absorbable" is a term which in the present context Is used to describe that the materials of which the said haemostatic compositions are made can be degraded in the body to smaller molecules having a size which allows them to be transported into the blood stream. By said degradation and absorption the said sponge materials will gradually be removed from the site of application. For example, gelatine can be degraded by proteolytic tissue enzymes to absorbable smaller molecules, whereby the gelatine sponge when applied in tissues typically is absorbed within about 3-6 weeks and when applied on bleeding surfaces and mucous membranes typically within 3-5 days.

In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means. In an interesting embodiment, the gelatine is prepared by denaturing collagen. Gelatine is typically prepared this way by denaturing collagen by chemical treatment with acids, bases, solvents, aldehydes, urea, or detergents such as sodium dodecyl sulphate and guanidine hydrochloride. By the above-mentioned denaturation procedure, the characteristics of the collagen molecule are modified, thereby resulting in an increase of water solubility.

Furthermore, the gelatine may be stabilised, which is considered advantageous in relation to the use of the sponge as a haemostat, the mechanical strength of the structure being greatly increased as compared to a non-stabilised gelatine structure which when becoming moistened will become dissolved and thereby collapse. In contrast, a stabilised gelatine sponge will retain its structure for a considerable period of time after application to a bleeding site. Methods of stabilising such sponges include treatment with a chemical cross-linking agent or with dry heat as described in the subsequent paragraphs.

Even though gelatine, in particular prepared by denaturing collagen as defined above represents a particularly suitable embodiment of the present invention, it will be understood that other biodegradable materials currently used for haemostatic purposes, such as collagen, chitin, chitosan, alginate, cellulose, e.g. oxidised cellulose, regenerated oxidised cellulose, carboxymethylcellulose (CMC) or hydroxyethylcellulose (HEC), polyglycolic acid, polyacetic acid, derivatives thereof and mixtures thereof, said materials being in their native form or structurally modified, may also be used without being regarded as departures from the spirit and scope of the present invention.

As indicated previously, the advantageous properties of the haemostatic sponges of the present invention are attributed to the presence of HA, or derivatives thereof, in the sponge. Another inherent advantage of HA, or a derivative thereof, is the excellent biologically absorbable and biocompatible properties of the molecule.

HA is a natural heteropolysaccharide consisting of alternate residues of D-glucuronic acid and N-acetyl-D-glucosamine. It is a linear polymer having a molecular weight ranging from about 50 to about 13,000 kDa, depending on the source it is obtained from and on the method of preparation. HA is present in nature in the preicellular gels, in the fundamental substance of connective tissue in vertebrate organisms (of which it is one of the main components), in the synovial fluid of joints, in the vitreous humor and in the umbilical cord. HA plays an important role in the biological organism as mechanical support for the cells of many tissues such as the skin, the tendons, the muscles and the cartilage. It is the main component of the extracellular matrix, but it has other functions such as hydration of tissues, lubrication as well as cell migration and differentiation. A suitable molecular weight for the purposes described herein will be in the range of from 50 to 5,000 kDa, such as in the range of from 50 to 4,000 kDa, e.g. in the range of from 100 to 3,000 kDa. In a particular preferred embodiment of the invention, the HA, or a derivative thereof, has a molecular weight in the range of from 250 to 3,500 kDa, more preferably in the range of from 500 to 2,500 kDa, such as in the range of from 500 to 2,000 kDa.

Optionally, the HA molecule may be cross-linked, e.g. by chemical or physical means. In a is preferred embodiment of the invention the employed HA is pH neutral, i.e. an aqueous solution of the employed HA exhibits a pH value in the range of from 5 to 9, preferably in the range of from 6-8, in particular in the range of from 6.5 to 7.5, such as about 7. The HA used in the present invention may be extracted from any source, for example from rooster comb. Alternatively the HA may be obtained by fermentation.

Derivatives of HA include, for example, esters of HA, as well as the derivatives described in U.S. Pat. No. 5,356,883; U.S. Pat. No. 6,548,081; U.S. Pat. No. 4,851,521; U.S. Pat. No. 6,027,741; US 2003 181689; EP 1 095 064; EP 0 341 745; WO 02/18450 and WO 2004/035629. In addition, the term "derivative" is also intended to cover hyaluronate salt, including, but not limited to, sodium hyaluronate, potassium hyaluronate, magnesium hyaluronate and calcium hyaluronate.

Specific examples of HA derivatives include the following HA derivatives:

HA salified with organic and/or inorganic bases,

Hyaff®, i.e. HA esters with alcohols of the aliphatic, araliphatic, cycloaliphatic, aromatic, cyclic and heterocyclic series, with an esterification degree that may vary depending on the type and length of the alcohol used, Hyadd®, i.e. amides of HA with amines of the aliphatic, araliphatic, cycloaliphatic, aromatic, cyclic and heterocyclic series, with an amidation degree that may vary depending on the type and length of the amine used, Hyoxx®, i.e. percarboxylated HA derivatives obtained by oxidation of the primary hydroxyl group of the N-acetyl-D-glucosamine unit, deacetylates of HA, i.e. derived from deacetylation of the N-acetyl-D-glucosamine unit, and O-sulphated HA derivatives.

The haemostatic composition of the present invention may in particular contain at least 0.5% (w/w) of HA or a derivative thereof calculated on the basis of the total weight of the "water-free" composition, or at least 1% (w/w) of HA or a derivative thereof, or at least 2% (w/w) of HA or a derivative thereof, or at least 3% (w/w) of HA or a derivative thereof, or at least 5% (w/w) of HA or a derivative thereof, or at least 7% (w/w) of HA or a derivative thereof, or at least 8% (w/w) of HA or a derivative thereof, or at least 10% (w/w) of HA or a derivative thereof. In an interesting embodiment of the invention, the haemostatic composition of the invention comprises at least 15% (w/w) of HA or a derivative thereof, such as at least 20% (w/w) of HA or a derivative thereof, e.g. at least 25% (w/w) of HA or a derivative thereof, preferably at least 30% (w/w) of HA or a derivative thereof, such as at least 35% (w/w) of HA or a derivative thereof, e.g. at least 40% (w/w) of HA or a derivative thereof.

Analogously, the haemostatic sponge of the invention typically comprises at the most 99.5% (wow) of said biologically absorbable material, such as at the most 99% (w/w) of said biologically absorbable material, or at the most 95% (w/w) of said biologically absorbable material, or at the most 90% (w/w) of said biologically absorbable material, or at the most 85% (w/w) of said biologically absorbable material, such as at the most 80% (w/w) of said biologically absorbable material, e.g. at the most 75% (w/w) of said biologically absorbable material, preferably at the most 70% (w/w) of said biologically absorbable material, such as at the most 65% (w/w) of said biologically absorbable material, e.g. at the most 60% (w/w) of said biologically absorbable material.

As will be understood by the skilled person, a significant amount of the biologically absorbable material must, however, be present in the sponge in order to provide the sponge with satisfactory mechanical and structural properties, i.e. the amount of HA, or a derivative thereof, should preferably not be too high. Accordingly, in a preferred embodiment of the invention, the sponge comprises at the most 90% (w/w) of HA or a derivative thereof, such as at the most 80% of HA or a derivative thereof, e.g. at the most 70% (w/w) of HA or a derivative thereof, preferably at the most 65% (w/w) of HA or a derivative thereof, such as at the most 60% (w/w) of HA or a derivative thereof, e.g. at the most 55% (w/w) of HA or a derivative thereof, in particular at the most 50% (w/w) of HA or a derivative thereof.

It is well known that for some compounds water molecules may be bound to the compound even when the compound is regarded as being "dry" and solid. In the context of the present invention the term "water-free" means that there is no water present, i.e. that water is absent. Thus even such water molecules which may be bound to a compound, as described above are not included when the term "water-free" is used, e.g. the term "water-free compound" refers to a compound excluding any water molecules which may be bound. For the haemostatic sponge of the present invention some residual water, such as up to about 10% (w/w) may be present in the sponge. This residual water is, however, not calculated as part of the total weight of the sponge. This means that when the sponge is said to contain a specified weight percent of a certain component (such as the HA, a derivative thereof or the biologically absorbable material) this weight percent is calculated on the basis of the total water-free weight of the sponge, i.e. on the total weight of the sponge excluding any water which may be bound e.g. as described above.

In one embodiment of the present invention the haemostatic sponge is dry. In this context the term "dry" refers to a sponge which may comprise some residual water but where the content of water in the sponge is in equilibrium with the water in the air. Thus the content of water is less or equal to the amount of water which can be present when it is in equilibrium with the water in the air.

In the currently most preferred embodiment of the invention, the HA, or a derivative thereof, is incorporated in the haemostatic sponge. By the term "incorporated" is to be understood that the HA molecules are located more or less uniformly in the reticulate sponge structure, preferably in such a way that no or only few "hot spots" of the HA molecules can be found in the sponge. The presence of "hot spots" does not have any effect on the functionality of the sponge. Thus, the term "incorporated", when used herein, may be used synonymously with expressions like "absorbed", "admixed" and the like.

In another embodiment of the invention, the HA, or a derivative thereof, is applied to one or more of the surfaces of the sponge. In a preferred embodiment, the HA, or derivative thereof, is applied to the surface intended for being in direct contact with the bleeding site, i.e. in a preferred embodiment the HA, or a derivative thereof, is applied to only one, two or three of the surfaces of the sponge. It will be understood that when the HA, or a derivative thereof, is applied to one or more of the surfaces of the sponges, the major part of the HA, or a derivative thereof, will be located on said surface(s). Nevertheless, a certain amount of HA, or a derivative thereof, may end up being incorporated into the sponge as the pore size of the sponge may be so that when a layer of HA, or a derivative thereof, is applied to the surface(s) of the sponge, the molecules of the HA, or a derivative hereof, may partially penetrate into the pores of the sponge.

Even though HA, or derivatives thereof, represents a particularly suitable embodiment of the present invention, it will be understood that other polysaccharides with properties similar to HA may be used in the present invention without being regarded as departures from the spirit and scope of the present invention. Examples of polysaccharides which may substitute HA, or derivatives thereof, in the sponges of the invention, include the mucopolysaccharides, such as chitin, chitosan, chondroitin sulphate, dermatan sulphate, keratan sulphate as well as alginate.

As explained above, one particular advantage of the haemostatic sponge of the invention is the anti-adhesive properties of HA, or a derivative thereof, which in turn has the advantage that post-operative adhesion of tissues may be avoided as explained in, e.g. U.S. Pat. No. 5,548,081 and in Laurent et al. *Am J Otolaryngol;* 7:181-186, 1986.

The main advantage of the haemostatic sponges of the present invention is, however, their ability to provide an efficient haemostatic action while, at the same time, possessing a reduced tendency to swell. Swelling of haemostatic sponges may be measured by various methods. For example, the swelling tendency may be expressed as the sponge's capability to absorb water; the more water absorbed, the more swelling (the greater volume) is obtained.

As will be apparent from the experiments provided herein, the haemostatic sponge of the invention has a reduced tendency to swell, i.e. to absorb water, when determined in accordance with USP 24. Accordingly, a preferred haemostatic sponge of the invention absorbs less water, i.e. it swells to a lesser extent than an absorbable gelatine sponge, such as Surgifoam®. More particularly, in a preferred embodiment of the invention, the ratio between the water absorbed by the haemostatic sponge of the invention and the water absorbed by an absorbable gelatine sponge, such as Surgifoam®, is at the most 0.95 when determined in accordance with USP 24. More preferably, the ratio is at the most 0.90, such as at the most 0.85, or at the most 0.80, or at the most 0.75, such as at the most 0.70, e.g. at the most 0.65, even more preferably at the most 0.60, such as at the most 0.55, in particular at the most 0.50.

Alternatively, the swelling properties may be assessed by soaking the haemostatic sponge in an excessive amount of distilled water. The sponge is subsequently picked up and air-dried for 10 minutes in order to drain out excess free water. The weight of the sponge before and after water absorption is used for calculating the swelling ratio: Swelling ratio=$(m_f - m_i)/m_i$, where $m_f$ is the weight of the sponge after soaking and removing of excess water, and $m_i$ is the initial weight of sponge before soaking.

Alternatively or in addition to the above tests, one may measure the expanding volume of a sponge in a graduated cylinder with distilled water; A known weight and volume of a sponge is pre-wetted and kneaded and quantitatively poured into the cylinder. The expanded volume is then measured and divided by the initial mass of the sponge, i.e. the weight of the sponge before pre-wetting.

In a preferred embodiment of the invention, the sponge further comprises at least one blood coagulation factor, such as a blood coagulation factor selected from the group consisting of thrombin or a precursor thereof, factor Va, factor VIa, factor VIIa, factor IXa, factor Xa, factor XIa, factor XIIa, factor XIIIa and calcium ions. In a highly preferred embodiment of the invention, said blood coagulation factor is thrombin or a precursor thereof, in particular thrombin itself. As seen from the examples the presence of thrombin in a sponge of the present invention decreases the time to haemostasis further. The thrombin may be plasma-derived, typically from a mammal source, such as a human. Alternatively, the thrombin may be produced by recombinant means.

Thrombin as well as precursors thereof may be incorporated into a haemostatic sponge by conventional means known to the person skilled in the art and as carefully explained in WO 90/13320.

In case thrombin or a precursor thereof is incorporated into the sponge of the invention, the sponge preferably further comprises a thrombin-stabilising agent, such as a thrombin-stabilising agent selected from the group consisting of naturally occurring amino acids, mono- or disaccharides, polyglycols, proteins and mixtures thereof.

By naturally occurring amino acids are understood any amino acid which is found in biologically produced proteins, including essential and non-essential dietary amino acids in their two stereoisomeric forms, such as arginine, histidine, isoleucine, leucine, lysine, methionine, phenylalanine, threonine, tryptophan, valine, alanine, aspartate, cysteine, glutamate, glycine, proline, serine, tyrosine, glutamine, and asparagine. Preferred amino acids are selected from the group consisting of glycine, lysine and arginine.

Suitable monosacchandes may be selected from D or L-forms of pentoses, such as ribose, arabinose, xylose, and lyxose and hexoses such as allose, altrose, glucose, mannose, gulose, idose, galactose, talose and derivatives thereof, e.g. pentosamines, hexosamines and glucoronic acid. Disaccharides may be selected from lactose, saccharose, maltose, fructose, and cellubiose, including derivatives thereof.

In a preferred embodiment of the sponge of the invention, a polyvalent alcohol is used as a thrombin-stabilising agent. A suitable polyvalent alcohol may be selected from ethylene glycol, diethylene glycol, propylene glycol, glycerol, mannitol, inositol, xylitol, erythritol, pentaerythritol, pentitols, hexitols, such as sorbitol, and heptitols. Furthermore, polyglycols, such as polypropylene glycol and polyethylene glycols may be useful as thrombin-stabilising agents. Among the latter group of compounds polyethylene glycols having a molecular weight in the range of 400-20,000, such as about 6,000 are preferred.

In an interesting embodiment of the invention, the HA, or derivative thereof, exerts in itself a thrombin-stabilising effect, in which case the haemostatic sponge does not contain any further thrombin-stabilising agents.

The mammalian body has an innate fibrinolytic system which is activated by deposition of fibrin. By dissolving fibrin, this system helps keep open the lumen of an injured blood vessel. However, in a situation where rapid haemostasis is aimed at, the fibrinolytic activity may counteract the haemostatic effect of a haemostatic adjunct, such as a haemostatic sponge according to the present invention. The fibrinolytic system involves the activation of plasminogen, a plasma precursor for an active proteolytic enzyme, plasmin, which is bound to lysine residues on the fibrin. Accordingly, it may be advantageous to have agents incorporated in the haemostatic sponge of this invention, which have an anti-fibrinolytic effect. Specific examples include an anti-fibrinolytic agent selected from the group consisting of aprotinin, pepstatin, leupeptin, antipain, chymostatin, gabexate mesilate, fibronectin, ε-amino caproic acid and tranexamic acid. Most preferably, the anti-fibrinolytic agent is ε-amino caproic acid or tranexamic acid, in particular tranexamic acid.

In addition, the haemostatic sponge of the invention may contain a buffering agent. Examples of buffering agents include alkaline metal salts, such as acetates, citrates, phosphates, hydrogen phosphates, carbonates, hydrogen carbonates, and succinates. Other useful buffering agents include imidazole, TRIS, and zwitteranionic buffering systems. Evidently, mixtures of the above-mentioned buffering agents may also be used.

Due to the superior swelling properties of the sponges describe herein, it will be appreciated that the sponge in addition to, or as an alternative to, providing a haemostatic effect, also may be used for local delivery of desirable agents, thereby using the sponge as a delivery vehicle or matrix. The desirable agent may be incorporated in the sponge or applied to one or more of the surfaces of the sponge in a conventional way, e.g. by soaking, dipping, spraying the sponge of the invention in or with a solution of the desirable agent or by other methods known to the skilled person. This can, e.g., be done by the clinician prior to use of the product by the clinician, or by the manufacturer.

Accordingly, in another aspect the present invention relates to a sponge comprising a biologically absorbable material and hyaluronic acid (HA) or a derivative thereof, wherein said sponge further comprises at least one desirable agent, in particular a desirable agent selected from the group consisting of surfactants, antimicrobial agents, antibacterial agents such as antiseptics and antibiotics, pain relieving agents, chemotherapeutics, anaesthetics, healing-promoting agents, vitamins, minerals, amino acids, proteins, growth factors, cells, enzymes, contrast agents, preservatives, emulsifiers, cross-linking agents to promote healing, etc.

In yet another aspect, the present invention relates to the use of a sponge comprising a biologically absorbable material and hyaluronic acid (HA) or a derivative thereof, wherein said sponge further comprises at least one desirable agent, for local delivery of said desirable agent.

In still another aspect, the present invention relates to a method for local delivery of a desirable agent to a patient in need thereof, said method comprising placing a sponge comprising a biologically absorbable material and hyaluronic acid (HA) or a derivative thereof, wherein said sponge further comprises at least one desirable agent, at the local site of the patient where said desirable agent is intended to be delivered. Thus the sponge comprising a biologically absorbable material and HA or a derivative thereof may in particular be used as a vehicle for delivery of an agent.

The term "local site" is intended to mean a part of a patient's body, in particular internal organs, such as a kidney, spleen, heart, etc.

In particular said desirable agent may be an antimicrobial agent. The antimicrobial agent may be selected from bactericidal or bacteriostatic agents, such as antibiotics and sulphonamides, antiviral compounds, antimycotic agents and anti-infectives. Antibiotics may be selected from e.g. β-lactams, penicillins, cephalosporins, monobactams, macrolides, polymyxins, tetracyclines, chloramphenicol, thrimethoprim, aminoglycosides, clindamycin, and metronidazole; sulphonamides may for example be selected from sulphadimidine or sulphadimethoxin; antimycotic agents may be selected from amphotericin B, ketoconazol and miconazol; and antiviral agent from idoxuridine andazidothymidin. Suitable antinfectives may for example be selected from halogens, chlorohexidine, quaternary ammonium compounds and triclosan. Other examples of bactericidal or bacteriostatic compounds include silver ions, in particular in the form of silver ion complexes. Another example of a suitable antimicrobial agent is tobramycin which in particular may be used as a salt thereof such as tobramycin sulphate.

The desirable agent may also be a chemotherapeutic such as Carboplatin.

Surfactants may be selected from the group consisting of anionic surfactants, cationic surfactants, non-ionic surfactants and surface active biological modifiers.

Examples of anionic surfactants include surfactants selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose. In particular sodium lauryl sulfate is preferred.

Examples of cationic surfactants include surfactants selected from the group consisting of quaternary ammonium compounds, benzalkonium chloride, cetyltrimethylammonium bromide, chitosans and lauryldimethylbenzylammonium chloride.

Examples of non-ionic surfactants include surfactants selected from the group consisting of polyoxyethylene fatty alcohol ethers, polyoxyethylene sorbitan fatty acid esters, polyoxyethylene fatty acid esters, sorbitan esters, glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

Examples of biological surfactants include, e.g., albumin and casein.

Examples of preservatives include benzoic acid, sorbic acid, parabens (e.g. methyl-p-hydroxy benzoic acid, ethyl-p-hydroxy benzoic acid, propyl-p-hydroxy benzoic acid, butyl-p-hydroxy benzoic acid and mixtures thereof), benzyl alcohol, chlorhexidine or benzalkonium chloride.

In an interesting embodiment of the invention, the haemostatic sponge of the invention is equipped with a top sheet, i.e. at least one of the surfaces of said haemostatic sponge may be covered by a top sheet. In one embodiment the top-sheet is not biodegradable. In one embodiment of the invention, the top sheet is removable and constructed from a thin plastic film of e.g. polyethylene, polypropylene or other materials which are substantially water-impervious. The skilled person will be aware of other suitable materials having the desired and required mechanical properties for this purpose. As will be understood, such top sheets are typically not biodegradable and should subsequently be removed. The materials mentioned above are typically transparent which, in turn, may give rise to problems in identifying the top sheet under and/or after surgery, in particular if the surgical area is covered or filled with a substantial amount of blood. Evidently, this increases the risk that the surgeon, or the staff assisting him, overlooks the presence of the top sheet. As will be understood, in case such a non-biodegradable top sheet is left in the body this may give rise to a severe clinical condition for the patient in question. Accordingly, in a preferred embodiment of the invention, a dye is incorporated in or on the top sheet, or part of the top sheet, thereby improving the visibility of the top sheet.

In another, and even more preferred, embodiment of the invention, the top sheet is prepared from a biodegradable material. Examples of suitable biodegradable materials include, for example, the polymeric materials mentioned in WO 2004/028583, page 6, line 3 to page 7, line 32, which is incorporated herein by reference. It will be understood that in this case the top sheet needs not necessarily be removed after surgery but may be left in the body.

The sponges of the invention may be prepared in any desirable shape and/or dimension depending on the intended use and the available process equipment. Typically, however, the thickness of the sponge of the invention will be in the range of 1-20 mm, such as in the range of 2-10 mm. Preferably, the thickness of the sponge is not less than 1 mm.

The haemostatic sponge is preferably subjected to a sterilisation treatment. Preferred methods of sterilisation include exposing the sponge to dry heat, ethylene oxide (EtO) or radiation, however other methods of sterilisation may be foreseen. Sterilisation with dry heat may typically be carried out by heating the sponges at a temperature between 110-200° C. In particular the temperature may be in the range of 110-160° C., e.g. in the range of 110-140° C., or in the range of 120-180° C., or in the range of 130-170° C., or in the range of 130-160° C., or in the range of 120-150° C. Furthermore, the period of time may in particular before a period between 15 minutes to 6 hours, such as between 14 hours, e.g. between 1.5-3 hours, or between 24 hours.

Methods for sterilisation with EtO are known to a person skilled in the art.

In yet another embodiment the sterilisation may be carried out by application of radiation, such as beta-or gamma-radiation. The dose typically lies in the range of 10-60 kGy, e.g. 20-60 kGy or 25-50 kGy, or 15-25 kGy, or 15-20 kGy, in particular around 15 kGy, 20 kGy or 25 kGy. Such treatment will reduce the bioburden of the sponge, and may also add to cross-linking of the molecular chains in the product.

In a particular embodiment the haemostatic sponge of the present invention has not been treated with a chemical cross-linking agent to stabilise the sponge but instead it has been treated with dry heat as described below. Thus in a preferred embodiment the haemostatic sponge of the present invention does not comprise a chemical cross-linking agent. The term chemical cross-linking agent is to be understood as any compound which is capable of stabilising a sponge of a biologically absorbable material. Such compounds are sometimes referred to as "activating agents". Different compounds have been used to chemically cross-link such sponges and include but are not limited to aldehydes, in particular glutaraldehyde and formaldehyde, acyl azide, caboiimides, hexamethylene diisocyanate, polyether oxide, 1,4-butanedioldiglycidyl ether, tannic acid, aldose sugars, e.g. D-fructose, genipin and dye-mediated photo-oxidation. Specific compounds include but are not limited to I-(3-dimethylaminopropyl)-3-ethylcarboiimide hydrochloride (EDC), dithiobis(propanoic dihydrazide) (DTP), I-ethyl-3-(3-dimethylamino-propyl)-carbodiimide (EDAC), Thus in a preferred embodiment of the present invention the haemostatic composition has not been treated with one of the above-mentioned chemical cross-linking agents, i.e. the haemostatic composition does not comprise any of the above-mentioned chemical cross-linking agents or residues thereof present as a result of having been used to stabilise the composition.

As indicated above, the haemostatic sponge of the invention may be used as a medication. In particular, the haemostatic sponge of the invention may be used for a haemostatic adjunct, or in the preparation for a haemostatic adjunct, in medical, veterinary or dental surgery. Accordingly, in a further aspect the present invention relates to a method of promoting haemostasis in a patient in need thereof, said method comprising applying a haemostatic sponge of the invention onto at least a portion of the area where bleeding occurs. In a still further aspect the present invention relates to a method for arresting bleeding comprising applying to the site of bleeding a haemostatic sponge according to the invention.

Before applying the haemostatic sponge to the surface, it is typically wetted in a saline solution. The inventors of the present invention have found that sponges which have been wetted before application have a lower time to haemostasis than when the same sponges are applied in dry form, i.e. without wetting the sponges before application. Thus in a preferred embodiment said sponge is wetted before it is applied to the surface. The haemostatic sponge may then subsequently be applied directly to surfaces and optionally, after being applied to the surface, held in place by pressure, e.g. by means of pads, dressings, webs, films, etc. or by other materials normally used in the medical practice. A preferred material for holding the sponge in place after being applied to the surface is surgical gauze or cotton gauze, optionally wetted in saline.

The haemostatic sponge of the invention may be used in an array of surgical procedures wherein bleeding control is desired, such as in orthopaedic procedures, e.g. in connection with laminectomy, total hip replacement and hip revisions, knee surgery, spinal fusion, etc.; in cardiothoracic/cardiovascular procedures, such as in connection with CABGs, valve replacements, aotic surgery, abdominal aortic aneurisms, carotid endarterectomy and femoral-popliteal bypass, amongst others.

In another embodiment the haemostatic composition of the present invention is in the form of a powder or flakes. Such a composition is intended to include a composition comprising a powder or flakes of a biologically absorbable material and a powder or flakes of hyaluronic acid or a derivative thereof, i.e. a composition wherein the individual powder granules or flakes either comprises a biologically absorbable material or hyaluronic acid or a derivative thereof. Such compositions are furthermore intended to include compositions wherein the individual powder granules or flakes comprise both a biologically absorbable material and hyaluronic acid or a derivative thereof.

Thus in a further aspect the original shape of the haemostatic sponges of the invention may be modified. For example, the sponge of the invention may be milled to a powder or flakes by methods known in the art, e.g. by means of rotary bed, extrusion, granulation and treatment in an extensive mixer, milling (e.g. by using a hammer mill or a centrifugal mill), or spray drying. Such powders or flakes may be used "as is" or may be pre-wetted with a liquid, such as saline, before use, thereby creating a paste.

The term "paste" may be used interchangeable with words like "gel", "suspension" and the like. In the present context, the term "paste" refers to a solid or semi-solid disperse system wherein the biologically absorbable material is dispersed in a liquid medium. The biologically absorbable material may also be referred to as a gel- or paste-forming agent. Furthermore, a paste is characterised by having a dynamic viscosity above that of water.

The paste may be obtained by suspending the particles of the biologically absorbable material (described above) in a liquid medium, in particular in an aqueous medium. Typically, about 1-20 ml liquid medium is employed per gram biologically absorbable material. The liquid medium is preferably an aqueous medium. More preferably the aqueous medium contains salts, such as sodium chloride, dissolved therein. Most preferably, the aqueous medium is saline.

Accordingly, in a further aspect the present invention relates to a powder composition comprising a biologically absorbable material and hyaluronic acid (HA) or a derivative thereof.

A still further aspect of the present invention relates to a paste comprising water, a biologically absorbable material and hyaluronic acid (HA) or a derivative thereof. It will be understood that the weight percentages given is calculated on the basis of only solid material in the paste.

Details and particulars concerning the powder and paste aspects will be the same as for the sponge aspect discussed above, and it means that whenever appropriate, the statements concerning amounts of HA, or a derivative thereof, present in the sponge, additional components present in the sponge, etc., will apply mutatis mutandis to the powder and paste aspects of the invention.

In further aspects the present invention relates to methods for preparing the haemostatic compositions of the invention.

In a particular embodiment the present invention relates to a method of producing a haemostatic composition comprising the steps of:
i) mixing a biologically absorbable material, hyaluronic acid or a derivative thereof and solvent ii) treating the mixture obtained in step i) with dry heat at a temperature between 110-200° C.

Hyaluronic acid is generally considered to be unstable at high temperatures. It was therefore a surprise when the inventors of the present invention found that a sponge comprising hyaluronic acid prepared according to the above-mentioned method had a higher reduction in the bleeding intensity than a similar sponge without hyaluronic acid (as shown in example 6). Thus indicating that the HA was active even though it had been treated with dry heat.

In the context of the present invention the term "dry heat" refers to the fact that the treatment is conducted without the presence of a saturated water vapour. Typically treatments at these temperatures are distinguished as being in the presence of a saturated water vapour, e.g. autoclaving, or without the presence of a saturated water vapour, i.e. with dry heat. The relevant period of time to treat the mixture with dry heat in step ii) depends on the temperature but may typically be in the range of 15 minutes to 6 hours, such as in particular between 30 minutes and 4 hours, e.g. between 14 hours, or between 1-3 hours or between 1-2 hours.

The step of treating the mixture with dry heat has a number of functions including:
a) Stabilisation of the three-dimensional structure of the mixture
b) Sterilisation
c) Removal of endotoxins The function of stabilisation is in particular important for haemostatic sponges because it makes the sponges less prone to disintegration and thereby affects the ability to handle the sponges.

The function of sterilisation and removal endotoxins is of course important for all forms of haemostatic compositions.

Said method may in a further embodiment comprise a further step of drying the mixture obtained in step i) before treating it according to step ii)

Details and particulars concerning how to mix the biologically absorbable material and hyaluronic acid or a derivative thereof and a solvent and how to dry the haemostatic composition may be performed as described below for the other methods of the present invention.

The present invention also relates to a haemostatic composition obtainable by the above-mentioned method. Previously chemical agents have been used to cross-link haemostatic sponges. An advantage of a haemostatic composition obtainable by the above-mentioned method is that it does not involve the use of a chemical cross-linking agent; hence residues of chemical agents in the composition are avoided.

It is to be understood that the details and particulars concerning the aspects of the haemostatic composition obtainable by the above-mentioned will be the same as for the sponge and powder and flakes aspects discussed above, and this means that whenever appropriate, the statements concerning the biologically absorbable material, amounts of HA, or a derivative thereof, present in the sponge, additional components present in the sponge, the form of the composition, etc., will apply mutatis mutandis to the aspects of the haemostatic composition obtainable according to the above-mentioned method.

The haemostatic composition comprising a biologically absorbable material and hyaluronic acid (HA) or a derivative thereof may be prepared by a number of different methods, which may depend on the form of the haemostatic composition, e.g. whether it is in the form of a sponge or a powder or flakes. Other aspects such as whether the hyaluronic acid is to be applied to a sponge or whether it is an integrated part of the sponge may also affect the choice of production method.

Hence if the haemostatic composition comprising a biologically absorbable material and hyaluronic acid (HA) or a derivative thereof is in the form of a sponge, said sponge may be prepared by one of the following methods although other methods of production are foreseen.

Thus in one embodiment the present invention also relates to a method for preparing a haemostatic sponge comprising a biologically absorbable material and hyaluronic acid or a derivative thereof, said method comprising the steps of:
   i) Treating a sponge of a biologically absorbable material with dry heat at a temperature between 110-200° C.
   ii) soaking the sponge obtained in step i) in hyaluronic acid or a derivative thereof Step i) treating the sponge with dry heat may be carried out as described above. Without being bound by any theory the inventors of the present invention believe that by soaking the sponge into a solution of HA or a derivative thereof said HA or derivative thereof becomes an integral component of the sponge in contrast to method in which a solution of HA or a derivative thereof is applied to one or more surfaces of said sponge. However, this may of course depend on how long the sponge is soaked in the solution. Hence if the sponge is only soaked very briefly in the HA or a derivative thereof solution it may be similar to applying it to one or more surfaces of the sponge.

In a preferred embodiment said method may comprise a further step of drying the sponge obtained in step ii). Said drying may be performed as described below.

In another embodiment, the present invention relates to a method for preparing a haemostatic sponge comprising a biologically absorbable material and hyaluronic acid (HA) or a derivative thereof, wherein said HA, or a derivative thereof, is incorporated in said sponge, said method comprising the steps of:
   i) mixing a biologically absorbable material, hyaluronic acid or a derivative thereof and solvent;
   ii) drying said mixture.

Said method may in one embodiment further comprise a step of stabilising the mixture obtained in step ii). Such methods of stabilisation include any of those methods described below, e.g. stabilisation with dry heat or with a chemical cross-linking agent.

In a particular embodiment of any of the above-mentioned methods the mixing of the biologically absorbable material, hyaluronic acid or a derivative thereof and solvent may be performed by any of the following alternatives:
   a) mixing a biologically absorbable material with hyaluronic acid or a derivative thereof and then subsequently adding a solvent
   b) mixing a solution of a biologically absorbable material with a solution of hyaluronic acid or a derivative thereof
   c) mixing a biologically absorbable material with a solution of hyaluronic acid or a derivative thereof
   d) mixing a solution of a biologically absorbable material with hyaluronic acid or a derivative thereof.

Furthermore, said mixing may in particular be performed under mechanical influence, such as whipping, stirring, spinning, static mixing, motionless mixing or centrifugation.

A number of different static mixing systems exists, e.g. from Bollin Dale which design and manufacture a range of static mixing systems for blending of a single product. Static mixing is sometimes also called motionless mixing. By the application of a dosing system and inline injectors, colours, flavouring or acids can be introduced into the product flow.

Thus the method for preparing a haemostatic sponge comprising a biologically absorbable material and hyaluronic acid (HA) or a derivative thereof, wherein said HA, or a derivative thereof, is incorporated in said sponge, may in particular comprise the following steps:
   i) providing a whipped or foamed solution of a biologically absorbable material, which may in particular be selected from the group consisting of gelatine, collagen, chitin, chitosan, alginate, cellulose, e.g. oxidised cellulose, oxidised regenerated cellulose, carboxymethylcellulose (CMC) or hydroxyethylcellulose (HEC), polyglycolic acid, polyacetic acid, derivatives thereof and mixtures thereof;
   ii) providing a solution of HA or a derivative thereof;
   iii) mixing the solutions provided in i) and ii) above; and
   iv) drying said mixture.

Said method for preparing a haemostatic sponge comprising a biologically absorbable material and hyaluronic acid (HA) or a derivative thereof, wherein said HA, or a derivative thereof, is incorporated in said sponge, may in particular further comprise a step of stabilising the sponge.

In a preferred embodiment of the present invention the above-mentioned solvent and/or solution is an aqueous solution. Said aqueous solution may in particular further comprise one or more salts, buffers or other suitable compounds, such as any of those described above.

The preferred biologically absorbable material is gelatine.

It is in some cases necessary to foam, whip or subject the solution to other mechanical forces, so that the desirable texture is obtained. In a preferred embodiment of the invention, the texture of the whipped or foamed solution resembles that of whipped cream. A suitable concentration of the biologically absorbable material will depend on the material of choice, but will typically be in the range of from 5 to 30% (w/v), such as in the range of from 10 to 20% (w/v). The temperature is preferably kept in the range of from 25° C. to 60° C., more preferably in the range of from 35° C. to 55° C.

In a preferred embodiment said mixing may be performed according to embodiment b), i.e. by mixing a solution of a biologically absorbable material with a solution of hyaluronic acid or a derivative thereof.

The solution of hyaluronic acid or a derivative thereof mentioned above may also preferably be provided in the form of a gel. The exact concentration of HA, or a derivative thereof, may largely depend on the HA or derivative used. Generally speaking, the solution should neither be too liquid, nor too viscous. The present inventors have found that good results are obtained using a concentration of from 1 to 5% (w/v), in particular of from 2 to 4% (w/v). In order to avoid cooling of the whipped or foamed solution of biologically absorbable material upon mixing, thereby potentially leading to an inhomogeneous mixture, the HA solution is preferably kept at an slightly elevated temperature, such as a temperature in the range of from 25° C. to 50° C., e.g. in the range of from 25° C. to 40° C., or in the range of from 25-35° C.

The mixing of the biologically absorbable material and a solvent is typically performed under mechanical influence in order to avoid clogging of the biologically absorbable material. Thus, during and/or immediately after mixing, the resulting mixture should preferably be whirled at high velocity, whipped, spinned, centrifuged or subjected to other kind of mechanical influence as will be known to the person skilled in the art. The solution of HA or a derivative thereof is subsequently mixed with said solution of the biologically material or a derivative thereof.

After mixing the resulting mixture may be poured into suitable trays or placed on finely perforated Teflon sheets or on sheets of silicon, e.g. with holes of an average diameter of 0.1-1.5 cm, such as around 0.4-0.6 cm, and drying is then performed at a temperature of from about 20-40° C. for a period of between 6 to 20 hours, in particular the temperature may be between 25° C. to about 35° C., such as about 30° C. The period of time may in particular be for about 12 to about 24 hours, typically for about 16 hours. If desired, the resulting sponge material may be stabilised by treating it with dry heat at elevated temperatures, such as in the range of from about 110° C. to 200° C. The stabilising time depends on the temperature, but will typically be from about 15 minutes to 6 hours. Stabilisation with dry heat may be carried out as described above.

In an alternative embodiment, the sponge is prepared by freeze-drying a mixture of the two solutions.

In still another aspect the present invention relates to a method for preparing a haemostatic sponge comprising a biologically absorbable material and hyaluronic acid (HA) or a derivative thereof, wherein said HA, or a derivative thereof, is applied to one or more of the surfaces of the sponge, said method comprising the steps of:
i) providing a sponge comprising a biologically absorbable material;
ii) providing a solution of HA or a derivative thereof;
iii) applying said solution of HA, or a derivative thereof, to one or more of the surfaces of the sponge; and
iv) drying the resulting sponge.

Said method may in one embodiment further comprise a step of stabilisation of the sponge, said stabilisation may in particular be carried out after one or more of the following steps: i), iii) and/or iv). The method of stabilisation may be any of those described below and includes but are not limited to treating it with dry and/or with a chemical cross-linking agent.

In particular the biologically absorbable material may be selected from the group consisting of gelatine, collagen, chitin, chitosan, alginate, cellulose, e.g. oxidised cellulose, regenerated oxidised cellulose, carboxymethylcellulose (CMC) or hydroxyethylcellulose (HEC), polyglycolic acid, polyacetic acid, derivatives thereof and mixtures thereof In a similar way as described above, the sponge is preferably a gelatine sponge, such as the commercially available Surgifoam® sponge. The HA solution as well as the drying step is preferably as discussed above. The HA solution may be applied to one or more of the surfaces of the sponge by any conventional technique known to the person skilled in the art. Application of the HA or a derivative thereof may performed by methods such as spraying or painting the sponge.

The haemostatic powder or flakes according to the present invention may in one embodiment be prepared by milling a sponge of a biologically absorbable material and then mixing it with a powder or flakes of HA or a derivative thereof.

In another embodiment it may be prepared by milling a sponge comprising a biologically absorbable material and hyaluronic acid or a derivative thereof. Milling of said sponges to a powder or flakes may be performed by methods known in the art, e.g. by means of rotary bed, extrusion, granulation and treatment in an intensive mixer, milling (e.g. by using a hammer mill or a centrifugal mill), or spray drying. Such powders or flakes may be used "as is" or may be pre-wetted with a liquid, such as saline, before use, thereby creating a paste. Preparation of such a paste may be performed as described above.

The sponges comprising a biologically absorbable material or a biologically absorbable material and HA or a derivative thereof may in particular have been stabilised.

The above-mentioned stabilisation step may unless stated otherwise be performed by any method. A preferred method of stabilisation of the sponges comprises heating the sponges at a temperature between 110-200° C. In particular the temperature may be in the range of between 110-160° C., e.g. in the range of between 110-140° C., or in the range of between 120-180° C., or in the range of between 130-170° C., or in the range of between 130-160° C., or in the range of between 120-150° C. The period of time depends on the temperature but may in particular be between 15 minutes and 6 hours, such as between 1-4 hours, e.g. between 1.53 hours, or between 2-4 hours.

However, other methods of stabilising such sponges include treating the sponges with a chemical cross-linking agent sometimes referred to as an activating agent.

Examples of such suitable cross-linking agents include but are not limited aldehydes, in particular glutaraldehyde and formaldehyde, acyl azide, caboiimides, hexamethylene diisocyanate, polyether oxide, 1,4-butanedioldiglycidyl ether, tannic acid, aldose sugars, e.g. D-fructose, genipin and dye-mediated photo-oxidation. Specific compounds include but are not limited to I-(3-dimethylaminopropyl)-3-ethylcarboimide hydrochloride (EDC), dithiobis(propanoic dihydrazide) (DTP), I-ethyl-3-(3-dimethylamino-propyl)-carbodiimide (EDAC).

The step of drying referred to in the above-mentioned methods may in particular be performed at a temperature of from about 20-40° C., typically for a period of between 6 to 20 hours, in particular the temperature may be between 25° C. to about 35° C., such as about 30° C. The period of time may in particular be for about 12 to about 24 hours, typically for about 16 hours.

The step of drying may in another embodiment be carried out by freeze-drying.

All of the above-mentioned methods may comprise a further step of sterilisation, wherein said step generally takes place after the steps of the above-mentioned methods. Preferred methods of sterilisation include exposing the haemostatic composition to dry heat, ethylene oxide (EtO) or radiation, however other methods of sterilisation may be foreseen. Sterilisation with dry heat may typically be carried out by heating the sponges at a temperature between 110-200° C. In particular the temperature may be in the range of 110-160° C., e.g. in the range of 110-140° C., or in the range of 120-180° C., or in the range of 130-170° C., or in the range of 130-160° C., or in the range of 120-150° C. Furthermore, the period of time may in particular be for a period of between 15 minutes to 6 hours, such as between 1-4 hours, e.g. between 1.5-3 hours, or between 2-4 hours.

In another embodiment sterilisation may be carried out by treating the sponge with EtO. Methods for sterilisation of such compositions with EtO are well known to a person skilled in the art.

In yet another embodiment the sterilisation may be carried out by application of radiation, such as beta- or gamma-radiation. The dose typically lies in the range of 10-60 kGy, e.g. 20-60 kGy or 25-50 kGy, in particular 20 kGy or 25 kGy. Such treatment will reduce the bioburden of the sponge, and may also add to cross-linking of the molecular chains in the product. In one embodiment of the present invention the haemostatic composition is stabilised by treating it with dry heat. This treatment may also have the function of sterilisation so for this embodiment the step of sterilisation may be the same as the step of stabilisation.

The inventors of the present invention have surprisingly discovered that sponges sterilised with dry heat or EtO appears to be more stable than sponges which have been sterilised with e-beam.

The present invention is further illustrated by the following, non-limiting, examples.

EXPERIMENTAL

In the following reference may be used interchangeably to the commercially available sponges Surgifoam® and Spongostan® which are the same.

Determination of Water Absorption According to USP 24

Cut a portion of about 10 mg from an absorbable gelatine sponge, weigh accurately, and place in a beaker of water. Knead gently between the fingers until thoroughly wet, and until all air has been removed, taking care not to break the tissue. Lift the portion of sponge from the water, and blot twice by pressing firmly between two pieces of absorbent paper. Drop the expressed sponge into a tared weighing bottle containing about 20 ml of water, and allow standing for 2 minutes. Lift the sponge from the water with a suitable hooked instrument, allow draining for 5 seconds, and discard the sponge. Again weigh the weighing bottle and water: the loss in water represents the weight of water absorbed by the sponge.

Porcine Spleen Model—Surgical Procedure

The pig was the animal of choice because it has a large blood volume and a large vascular spleen that enables many haemostatic comparisons on each animal. The test compositions were applied one after one to surgical incisions made in the spleen. Negative controls were performed at the start and at the end of each study by using saline-moistened gauze to demonstrate consistent bleeding of >12 minutes in the absence of a haemostatic agent.

The primary test parameter was the time to haemostasis or reduction in the bleeding intensity.

A midline abdominal incision was made to expose the spleen. Incisions, 10-15 mm long and 2 mm deep, were made into the spleen. The test composition (or control) was applied with digital pressure for 2 minutes, the composition was lifted, and evaluation of the bleeding intensity was conducted. Subsequently, evaluation of the bleeding intensity was conducted every 30 seconds for 5-7 minutes.

About 20 incisions were made in each pig spleen.

Example 1

Preparation of Sponge #1

A HA gel (2% (w/v)) was prepared from *Streptococcus Equi* sp hyaluronic acid sodium salt (Biochemika) with a molecular weight of 1,500-1,800 kDa. The gel was added to freshly foamed gelatine (16.7% (w/v)). Immediately after addition of HA, the mixture was whirled at high velocity to avoid clogging of the gelatine. In order to avoid an inhomogeneous mixture, the temperature should not be below room temperature. After mixing, the mixture was poured into trays or placed on finely perforated teflon sheets, followed by air drying at approximately 30° C. and 10% relative humidity for about 16 hours. Sponges prepared this way typically had a HA content of about 25-50% (w/w).

Example 2

Preparation of Sponge #2

A HA gel (2% (w/v)) was prepared from *Streptococcus Equi* sp hyaluronic acid sodium salt (Biochemika) with a molecular weight of 1,500-1,800 kDa. The gel was added to freshly foamed gelatine (16.7% (w/v)). Immediately after addition of HA, the mixture was whirled at high velocity to avoid clogging of the gelatine. In order to avoid an inhomogeneous mixture, the temperature should not be below room temperature. After mixing, the mixture was poured into trays or placed on fine perforated teflon sheets, followed by gentle freeze-drying (product temperature: 30° C. after 7 hours). Sponges prepared this way had a more porous structure as compared to the sponges prepared in Example 1. Moreover, it was found that this method was suitable for preparing sponges having a higher thickness.

Example 3

Preparation of Sponge #3

HA gel (2 (w/v)) was prepared from *Streptococcus Equi* sp hyaluronic acid sodium salt (Biochemika) with a molecular weight of 1,500-1,800 kDa. The gel was smeared on the upper surface of a gelatine sponge (Surgifoam®) followed by air drying at approximately 30° C. and 10% relative humidity for about 16 hours. Sponges prepared this way typically had a HA content of at least 13% (w/w).

Example 4

Determination of Water Absorption According to USP 24

Sponge #1 was subjected to the water absorption test (USP 24) described above. The USP 24 method is intended for absorbable gelatine sponges without HA. In the USP 24 method, kneading of the sponges has been optimised with respect to gelatine sponges. For the sponges of the invention, the kneading should preferably be more gentle.

The absorption properties were compared to a commercially available gelatine sponge Surgifoam®. The following results were obtained:

|  | Sponge #1<br>Relative absorption (g/g) | Gelatine sponge<br>Relative absorption (g/g) |
| --- | --- | --- |
|  | 30.4 | 60.0 |
|  | 29.5 | 57.9 |
|  | 27.1 | 50.0 |
|  | 24.1 | 54.9 |
|  | 25.1 | 59.9 |
| Mean: | 27.2 | 56.5 |
| SD: | 2.7 | 4.0 |

As can be seen, the ratio between the water absorbed by sponge #1 and the water absorbed by the absorbable gelatine sponge (Surgifoam®) was 27.2/56.5=0.48.

In addition, by visual inspection of the wetted sponges, it was evident that sponge #1 swelled to a significantly lesser extent than did the Surgifoam® sponge.

Example 5

Evaluation of Haemostatic Efficacy in a Porcine Spleen Model

The object of this study was to compare the efficacy of the sponges of the invention as compared to commercially available gelatine sponges (Surgifoam®) when applied to small, freely bleeding incisions made in the spleen of a pig. The sponges (6.5 cm$^2$) were applied after pre-wetting in sterile saline, followed by kneading as gently as possible.

The pig was the animal of choice since it has a large blood volume and a large vascular spleen that enables many haemostatic comparisons on each animal. The sponges were applied one after one to multiple surgical incisions in the spleen during the test period. The pigs were euthanized and not allowed to recover from anaesthesia.

The primary test parameter was time to haemostasis.

A midline abdominal incision was made to expose the spleen. 1.0 cm incisions (2 mm deep) were made in the spleen. Two incisions were made to demonstrate consistent bleeding with saline-moistened gauze and three incisions were made for each sponge to be tested.

The test sponge (or control) was applied with digital pressure for 2 minutes. Haemostasis evaluation occurred every 30 seconds with an additional 30 seconds of digital pressure. A negative control using saline-moistened gauze was performed at the start and at the end of the study to demonstrate consistent bleeding of >12 minutes in the absence of a haemostatic agent.

A trial was stopped if the bleeding did not stop within at least 5 minutes and/or if the sponge was saturated without reducing bleeding during the previous inspections.

The following results were obtained:

| Sponge | Time to haemostasis (min) | Surgeon's comments |
| --- | --- | --- |
| Negative control | >12 | |
| Gelatine sponge | >6 | Trial stopped because of saturated sponge and no reduced bleeding observed. The incision size was 1.5 cm in this trial. From this stage the incision size was reduced to 1.0 cm. |
| Gelatine sponge | >5 | Almost no bleeding. Trail stopped because of saturated sponge and no reduced bleeding was observed. |
| Gelatine sponge | >5 | Trail stopped because of saturated sponge and no reduced bleeding was observed. |
| Sponge #1 | 5 | Pre-wetting slow compared to Surgifoam ®. Good adherence to surface. Only superior absorption in the sponge. |
| Sponge #1 | 3 | Pre-wetting slow compared to Surgifoam ® and becomes less soft by pre-wetting. Only superior absorption in the sponge. |
| Sponge #1 | 2 | |
| Sponge #3* | >5.5 | Reduced to moderate bleeding. Trial stopped because of saturated sponge and no reduced bleeding was observed. |
| Sponge #3* | >5 | Trial stopped because of saturated sponge and no reduced bleeding was observed. Easy to pre-wet. |
| Sponge #3* | >5 | Almost no bleeding. Product saturated after 5 minutes. |
| Sponge #3** | 5 | Only superficial absorption in the sponge. |
| Sponge #3** | 5 | Slight absorption within the sponge. |
| Sponge #3** | 3 | Only superficial absorption in the sponge |
| Negative control | >12 | |

*HA layer away from bleeding
**HA layer towards bleeding
The reason for Surgifoam ® exhibiting a longer time to haemostasis than seen in previous porcine spleen models could be explained by the relative small size of the sponge (6.5 cm²).

As can be seen from the obtained results, the haemostatic properties of the sponges of the invention (sponge #1 and #3) were clearly superior as compared to Surgifoam®. In particular, sponge #1 was very efficient having a difference in mean time to haemostasis of at least 2 minutes as compared to Surgifoam®.

Example 6

Evaluation of Reduction of Bleeding Intensity in a Porcine Spleen Model

The following different compositions were tested:
A sponge of gelatine with and without HA (S4 vs. SI)
A sponge of oxidised cellulose with and without HA (S9 vs. S8)
A powder of gelatine with and without HA (S3 vs. S2)
A sponge of gelatine with thrombin (S7)

The SI sponge was a commercially available gelatine sponge Spongostan®.

The S4 sponge was prepared as described under example 1 and then subsequently treated with dry heat by placing it in a paper-bag in an oven at 150° C. for 90 min.

The S7 sponge was a Spongostan® sponge, which was further soaked in a 1000 U/mL thrombin-solution.

The S8 sponge was a commercially available sponge of oxidised cellulose, called Surgicel®.

The S9 sponge was prepared by wetting the commercially available sponge Surgicel® in a gel of HA until the concentration of HA in the sponge was 10% w/w. The sponge with HA was then subsequently freeze-dried.

The powder without HA (S2) was prepared by milling a Spongostan® sponge and just before application mixing the powder with saline to obtain a paste.

The powder with HA (S3) was prepared similarly by milling a Spongostan® sponge and then subsequently mixing the powder obtained by said milling with HA powder and then just before application adding saline to this mixture to obtain a paste.

In short, the haemostatic efficacy of the samples was evaluated by the following method:

An incision was made into the spleen and the intensity of the resulting bleeding was evaluated on a scale ranging from 0-5. Subsequently, the sample in question was applied to the incision and at predetermined intervals, the sample was lifted from the incision and the intensity of the bleeding was evaluated before the sample was reapplied. Powder samples and oxidised cellulose samples was not lifted from the incision which is very likely to affect the reduction in the bleeding intensity also for the compositions without HA. The bleeding intensity was in those cases evaluated by the amount of blood leaking through the samples. Each experiment was terminated after 7 minutes if haemostasis (0 on the scale) had not occurred before. 7 repetitions (distributed onto all four pigs) were performed for each type of sample, except for the reference samples for which 3 repetitions were performed on each pig, i.e. 12 repetitions in total.

The bleeding intensity reduction was calculated for each experiment as the difference between the evaluated bleeding intensities at the start and at the end of the experiment. The resulting averages of these numbers are shown in below Table.

Results:

| Sample | Average bleeding intensity reduction | Lifting of the composition from the incision for evaluation of the bleeding intensity |
| --- | --- | --- |
| S1: Gelatine sponge (Spongostan ®), heated at 150° C. for 180 min | 0.82 | Yes |

| Sample | Average bleeding intensity reduction | Lifting of the composition from the incision for evaluation of the bleeding intensity |
|---|---|---|
| S4: Gelatine sponge with 30% w/w HA (Biochemika), heated at 150° C. for 90 min | 4.29 | Yes |
| S7: Gelatine sponge (Spongostan ®) with thrombin | 3.00 | Yes |
| S2: Gelatine powder irradiated (e-beam) with 15 kGy | 2.86 | No |
| S3: Gelatine powder with 10% w/w HA (HTL) and irradiated (e-beam) with 15 kGy | 3.67 | No |
| S8: Sponge of oxidised cellulose (Surgicel ®) | 2.71 | No |
| S9: Sponge of oxidised cellulose (Surgicel ®) with 10% w/w HA (HTL) | 3.29 | No |

The results show that the presence of a gelatine sponge, a gelatine powder and a sponge of oxidised cellulose with HA reduce the bleeding intensity more than the same sponges and powder without HA (S4 vs. SI, S3 vs. S2 and S9 vs. S8).

Furthermore, the results also show that a gelatine sponge with HA results in a larger reduction in the bleeding intensity than a gelatine sponge with thrombin (S4 vs. S7).

In a similar study the reduction of the bleeding intensity of a Lyostypt collagen compress (commercially available) without HA or with 10% w/w HA was measured. For the Lyostypt collagen compress without HA the average reduction in the bleeding intensity was found to be 1.00, while for the Lyostypt collagen compress with 10% w/w HA it was found to be 1.43. Thus also for this type of haemostatic composition the presence of HA appears to improve the reduction in the bleeding intensity.

The Lyostypt collagen compress was not lifted from the incision for evaluation of the bleeding intensity.

Example 7

Evaluation of the Time to Haemostasis in a Porcine Spleen Model; Effect of Method of Application and the Presence of Thrombin in the Sponge The sponges were prepared as described in example 1. Subsequently each of the sponges was treated in the following manner:

Test sample B was moistened and kneaded in ajar with plenty of sterile saline for 30 seconds and squeezed before application. Test sample B was before application placed on pre-wetted gauze.

Test samples D and E were placed in a jar with 2 mL sterile saline. The sponge was kneaded very gently and turned upside down to make sure all the saline was absorbed within the whole sponge. After a maximum of 1 minute the bottom-side of the sponge was placed upside on the Parafilm topfilm and was ready for application.

Test samples F and G were placed in a jar with 2 mL Thrombin solution (1000 U/mL) and the sponges were kneaded very gentle and turned upside down to make sure all the Thrombin solution was absorbed within the whole sponge. After a maximum of 1 minute the bottom-side of the sponge was placed upside on the Parafilm topfilm and then it was ready for application.

Test samples J, and K) were applied dry.
Test sample L was wetted in saline as described for test sample D and E.

| Sponge | Time to haemostasis |
|---|---|
| B: Gelatine sponge (Surgifoam ®) wetted in saline | 3-5 minutes |
| D: Gelatine sponge with 30% w/w HA with a Mw of $2.18 \times 10^5$ Da wetted in saline | 2.5-3.5 min (average 3 min) |
| E: Gelatine sponge with 30% w/w HA with a Mw of $1.06 \times 10^6$ Da wetted in saline | 2.0-2.5 min (average 2.25 min) |
| F: Gelatine sponge with 30% w/w HA with a Mw of $2.18 \times 10^5$ Da wetted in 1000 units/ml thrombin | 2.0-3.0 (average 2.25 min) |
| G: Gelatine sponge with 30% w/w HA with a Mw of $1.06 \times 10^6$ Da wetted in 1000 units/ml thrombin | 2.0 min (average 2.0 min) |
| J: Gelatine sponge with 30% w/w HA with a Mw of $2.18 \times 10^5$ Da applied dry | 4.0-7.0 min (average 5.75 min) |
| K: Gelatine sponge with 30% w/w HA with a Mw of $1.06 \times 10^6$ Da applied dry | 5 min to 7 min |
| L: Gelatine sponge with 30% w/w HA from a fermented process and with a Mw of $1.5\text{-}1.8 \times 10^6$ Da wetted in saline | 2.0-2.5 min (average 2.25 min) |

The results show that when the sponges are applied wet the time to haemostasis appears to be shorter than when the sponges are applied dry (D vs. 3 and E vs. K).

Furthermore, wetting the sponges in thrombin appears to reduce the time to haemostasis even further than by wetting them in saline (F vs. D and G vs. E).

The higher molecular weight of HA also appears to reduce the time to haemostasis more than the lower molecular weight of HA (E vs. D and G vs. F).

Example 8

Use of a Sponge of the Present Invention as a Vehicle for Delivery of a Substance The present invention was compared to the commercially available Surgifoam® with respect of release of tobramycin sulphate.

Both preparations were cut into smaller sponges with a diameter of 14 mm and soaked in a solution of tobramycin sulphate. The release of tobramycin sulphate from the preparations serving as vehicles, were measured by quantification of tobramycin sulphate using an USP HPLC method. The actual release took place in Franz diffusion cells, and samples were taken after 0, 10, 30, 60, 120, 1440, 2880 and 3975 minutes. The amount of tobramycin sulphate was calculated on the basis of a standard solution.

The results were that the sponges comprising gelatin and HA had a tendency to release more tobramycin sulphate that the commercially available gelatin sponge did in the 3975 minutes the study ran.

Additionally a collagen sponge comprising 10% HA w/w was investigated in the same set up. As for the above, the results indicated that the release of tobramycin sulphate was greater from the collagen sponge with HA than from the gelatin sponge (Surgifoam®)

Furthermore the release of carboplatin from the present investigation, the collagen sponge with 10% HA w/w and the commercially available Surgifoam® was examined in a similar study. The results obtained with release of carboplatin con-firmed the tendency seen with tobramcyin that the preparations containing HA releases more of the test substance than the gelatin sponge does.

The results of the above indicate that the present invention and a collagen sponge comprising HA can be used as vehicles for different substances, and that their release seems to be greater than from a gelatin sponge.

The invention claimed is:

1. A sterile haemostatic composition comprising gelatin and hyaluronic acid (HA) or a salt thereof, wherein said gelatin and hyaluronic acid (HA) or a salt thereof is stabilized with dry heat at 110-200° C., and wherein said haemostatic composition does not comprise a chemical cross-linking agent or residues thereof.

2. The haemostatic composition according to claim 1, wherein said composition is in the form of a sponge, powder or flakes.

3. The haemostatic composition according to claim 2, wherein said composition is in the form of a haemostatic sponge and wherein said sponge absorbs less water than an absorbable gelatin sponge.

4. The haemostatic composition according to claim 1, wherein said composition comprises at the most 80% (w/w) of said gelatin.

5. The haemostatic composition according to claim 1, wherein said hyaluronic acid (HA) or a salt thereof is incorporated into said composition to a final content of at least 20% (w/w).

6. The haemostatic composition according to claim 1, wherein said dry heat treatment at 110-200° C. is conducted for 15 minutes to 6 hours.

7. The haemostatic composition according to claim 1, wherein said hyaluronic acid (HA) or a salt thereof is incorporated into said composition to a final content of at least 10% (w/w).

8. The haemostatic composition according to claim 3, wherein the ratio between the water absorbed by the haemostatic sponge according to claim 3 and the water absorbed by the absorbable gelatin sponge is at the most 0.95.

9. The haemostatic composition according to claim 1, wherein said composition is in the form of a haemostatic sponge, wherein at least one of the surfaces of the haemostatic sponge is covered by a top sheet.

10. The haemostatic composition according to claim 9, wherein the top sheet is removable.

11. The haemostatic composition according to claim 1, wherein said composition is dry.

12. A haemostatic paste prepared by pre-wetting the haemostatic composition according to claim 1 with a liquid to create a paste, wherein a haemostatic composition is in the form of a powder or flakes.

13. The haemostatic composition according to claim 1, wherein said composition comprises at the most 85% (w/w) of said gelatin.

14. The haemostatic composition according to claim 1, wherein said composition comprises at the most 75% (w/w) of said gelatin.

15. The haemostatic composition according to claim 1, wherein said composition comprises at the most 70% (w/w) of said gelatin.

16. The haemostatic composition according to claim 1, wherein said composition comprises at the most 65% (w/w) of said gelatin.

17. The haemostatic composition according to claim 1, wherein said composition comprises at the most 60% (w/w) of said gelatin.

18. The haemostatic composition according to claim 1, wherein said hyaluronic acid (HA) or a salt thereof is incorporated into said composition to a final content of at least 15% (w/w).

19. The haemostatic composition according to claim 1, wherein said hyaluronic acid (HA) or a salt thereof is incorporated into said composition to a final content of at least 25% (w/w).

20. The haemostatic composition according to claim 1, wherein said hyaluronic acid (HA) or a salt thereof is incorporated into said composition to a final content of at least 30% (w/w).

21. The haemostatic composition according to claim 1, wherein said hyaluronic acid (HA) or a salt thereof is incorporated into said composition to a final content of at least 35% (w/w).

22. The haemostatic composition according to claim 1, wherein said hyaluronic acid (HA) or a salt thereof is incorporated into said composition to a final content of at least 40% (w/w).

23. The haemostatic composition according to claim 1, wherein the hyaluronic acid (HA) is physically cross-linked.

24. The haemostatic composition according to claim 1, wherein the hyaluronic acid (HA) has a pH value in the range of from 5 to 9.

25. A method for producing a cross-linked and sterile haemostatic composition according to claim 1 comprising the steps of:
  i) mixing gelatin, hyaluronic acid or a salt thereof, and a solvent, and
  ii) treating the mixture obtained in step i) with dry heat at a temperature between 110-200° C.

26. The method according to claim 25, wherein said method comprises a further step of drying the mixture obtained in step i) before treating the mixture with dry heat at a temperature between 110-200° C. according to step ii).

27. A method for preparing the haemostatic composition according to claim 11, said method comprising the steps of:
  i) mixing gelatin, hyaluronic acid (HA) or a salt thereof, and a solvent;
  ii) cross-linking said composition with dry heat at 110-200° C.; and
  iii) drying said mixture.

28. A method according to claim 25, wherein the mixing of gelatine, hyaluronic acid (HA) or a salt thereof, and a solvent is performed by any of the following alternatives:
  a) mixing gelatine with hyaluronic acid (HA) or a salt thereof and subsequently adding a solvent;
  b) mixing a solution of gelatine with a solution of hyaluronic acid (HA) or a salt thereof;
  c) mixing gelatine with a solution of hyaluronic acid (HA) or a salt thereof;
  d) mixing a solution of gelatine with hyaluronic acid (HA) or a hyaluronate salt thereof.

29. The method according to any of claims 25 or 27, wherein said mixing is performed mechanically.

30. The method according to any of claims 25 or 27, wherein said hyaluronic acid (HA) or a salt thereof is provided in the form of a gel.

31. The method according to any of claims 26 or 27, wherein said drying is performed at a temperature from 20° C. to 40° C.

32. The method according to any of claims 26 or 27, wherein said drying is conducted for 6 to 24 hours.

33. The method according to any of claims 26 or 27, wherein said drying is performed by freeze-drying.

34. The method according to any of claims 25 or 27 wherein said mixing is performed by whipping, stirring, spinning, static mixing, motionless mixing or centrifugation.

* * * * *

UNITED STATES PATENT AND TRADEMARK OFFICE
CERTIFICATE OF CORRECTION

PATENT NO. : 8,021,684 B2  Page 1 of 1
APPLICATION NO. : 10/562831
DATED : September 20, 2011
INVENTOR(S) : Moller et al.

It is certified that error appears in the above-identified patent and that said Letters Patent is hereby corrected as shown below:

Title page, item (73) Assignee: The country of the Assignee "(DE)" should read --(DK)--.

Signed and Sealed this
Eighth Day of November, 2011

David J. Kappos
*Director of the United States Patent and Trademark Office*